United States Patent [19]

Kluepfel et al.

[11] Patent Number: 5,202,249
[45] Date of Patent: Apr. 13, 1993

[54] XYLANASE FOR BIOBLEACHING

[75] Inventors: Dieter Kluepfel, Montreal; Rolf Morosoli, Ville St-Laurent; Francois Shareck, Dollard-des-Ormeaux, all of Canada

[73] Assignee: Imperial Chemical Industries PLC, London, Great Britain

[21] Appl. No.: 744,570

[22] Filed: Aug. 13, 1991

[51] Int. Cl.$^5$ .............................................. C12N 9/26
[52] U.S. Cl. ................... 435/201; 435/69.1; 435/71.2; 435/172.3; 435/252.35; 435/278; 435/320.1; 435/886; 536/23.2; 935/14; 935/29; 935/56; 935/59; 935/75
[58] Field of Search ............ 435/201, 278, 69.1, 435/71.2, 320.1, 252.35, 172.3, 886; 536/27; 935/14, 29, 56, 59, 75

[56] References Cited

FOREIGN PATENT DOCUMENTS 2557894 7/1985 France .

OTHER PUBLICATIONS

Bernier et al. "Molecular Cloning of a *Bacillus subtillis* Xylanase Gene in Escherichia coli" Gene 26:59-65 (1983).
Zappe et al., "Nucleotide sequence of a Clostridium acetobutylicum P262 xylanase gene (xynB)", Nucleic Acids Research, vol. 18, No. 8 (1990).
Morosoli et al., "Purification and properties of a Xylase from Streptomyces lividans", Biochem. J. (1986) 239 587-592.
Bertrand et al., "Expression of the Xylanase Gene of Streptomyces lividans and Production of the Enzyme on National Substrates", Biotechnology Bioeng., vol. 33, pp. 791-794 (1989).
Iwasaki et al., "Molecular Cloning of a Xylanse Gene from Streptomyces SP. No. 36a and its expression in Streptomycetes", The Journal of Antibiotics, vol. 39, No. 7, p. 985 (1986).

Viikari et al., "Application of Enzymes in Bleaching"; Proceedings of the International Symposium on Wood and Pulping Chemistry; Paris (1987).
Mondu et al., "Cloning of the xylanase gene of streptomyces lividans", Gene, 49 (1986) 323-329.
Chauvet et al., "Assistance in bleaching of never-dried pulps by the use of Xylanases, consequences on pulp properties", Proceedings of the International Symposium on Wood and Pulping Chemistry, Paris (1987) p. 235.
Kluepfel, "Screening of Prokaryotes for Cellulose-and Hemicellulose-Degrading Enzymes", Methods in Enzymology, vol. 160, p. 180, (1988).
Vats-Mehta et al., "Cloning of a second xylanase-encoding gene of Streptomyces lividans 66"; Gene 86, 119, (1990).
Thompson et al., "Cloning of Antibiotic Resistance and Nutritional Genes in Streptomycetes", Mol. Gen. Genet; 195, 39, 1982.
Viikari et al.; "Bleaching with Enzymes"; 3rd Int. Conf. Biotechnology in the Pulp and Paper Industry, Stockholm 16-19.6, 1986, pp. 67-69, 1987.

(List continued on next page.)

Primary Examiner—Robert A. Wax
Assistant Examiner—Rebecca Prouty
Attorney, Agent, or Firm—William E. Dickheiser

[57] ABSTRACT

A process for the production and use of a xylanase enzyme, having a high specific activity, of use in the treatment and/or biobleaching of chemical pulps is described. The enzyme provides for a more commercially feasible process for the treatment of pulps, and lignocellulosic materials in general, which process provides improved results in delignification and brightening over conventional bleaching process, together with reduced bleaching chemical consumption and environmental impact.

10 Claims, No Drawings

OTHER PUBLICATIONS

Kendall et al.; "Cloning and expression of an extracellular-agarase gene from Streptomyces coelicolor A3(2) in Streptomyces lividans 66"; Gene, 29 (1984) pp. 315–321.

Chater et al., "Gene Cloning in Streptomyces"; Current Topics in Microbiology and Immunology, 97,69,1982.

Teather et al.; "Use of Cargo Red-Polysaccharide Interactions in Enumeration and Characterization of Cellulolytic Bacteria from Bovine Rumen"; Applied and Environmental Microbiology, Apr. 1982, pp. 777–780.

Sanger et al.; "DNA sequencing with chain-terminating inhibitors"; Proc. Natl. Acad. Sci. USA, vol. 74, No. 12, pp. 5463–5467, Dec. 1977.

Dale et al.; "A rapid Single-Stranded cloning strategy for Producing a sequential Series of Overlapping Clones for Use in DNA Sequencing:Application to Sequencing the Corn Mitochondrial 18 S rDNA"; Plasmid, 13, 31–40 (1985).

Hopwood et al.; "Genetic Manipulation of Streptomyces; A lab manual"; 1985, The John Innes Foundation, Norwich.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

( A ) LENGTH: 675 base pairs ( B ) TYPE: nucleic acid ( C ) STRANDEDNESS: Single strand ( D ) TOPOLOGY: Circular ( x i ) SEQUENCE DESCRIPTION: SEQ ID NO:1:

```
                                            CTGCTGCTGC CCGGCACAGC CCACGCC    360
GCCACTACCA TCACCACCAA CCAGACCGGC ACCGACGGCA TGTACTACTC GTTCTGGACC           420
GACGGCGGCG GCTCCGTCTC CATGACGCTC AACGGTGGCG GCAGCTATAG CACCCAGTGG           480
ACCAACTGCG GCAACTTCGT CGCCGGCAAG GGCTGGAGCA CCGGCGACGG CAACGTCCGC           540
TACAACGGCT ACTTCAACCC CGTCGGCAAC GGCTACGGCT GCCTCTACGG CTGGACCTCG           600
AACCCGCTGG TGGAGTACTA CATCGTCGAC AACTGGGGCA GTTACCGGCC CACCGGTACG           660
TACAAGGGCA CCGTCTCCAG CGACGGAGGC ACCTACGACA TCTACCAGAG GACCCGGTAC           720
AACGCCCCT   CCGTGGAAGG CACCAAGACC TTCCAGCAGT ACTGGAGTGT CCGGCAGTCG           780
AAGGTGACCA GTGGCTCCGG CACCATCACC ACCGGCAACC ACTTCGACGC CTGGGCGCGC           840
GCGGGCATGA ACATGGGCCA GTTCAGGTAC TACATGATCA TGGCCACCGA GGGCTATCAG           900
AGCAGTGGAA GCTCGAACAT CACGGTCAGC GGTTGACCTC TGGCCGGTGG ACGACGGGGC           960
GTGGGCCGTC TACGTGGCGG GCCAACAACT GTGGTCGCAT TGCTGGGA                       1008
```

(2) INFORMATION FOR SEQ ID NO:2:
    (i) SEQUENCE CHARACTERISTICS:
        (A) LENGTH: 200 amino acids
        (B) TYPE: Amino acid
        (C) STRANDEDNESS: Single strand
        (D) TOPOLOGY: Circular
    (xi) SEQUENCE DESCRIPTION: SEQ ID NO:2:

```
Leu Leu Leu Pro Gly Thr Ala His Ala Ala Thr Thr Ile Thr Thr Asn Gln Thr
 1           5                    10                  15

Gly Thr Asp Gly Met Tyr Tyr Ser Phe Trp Thr Asp Gly Gly Gly Ser Val Ser
     20              25                  30                  35

Met Thr Leu Asn Gly Gly GLy Ser Tyr Ser Thr Gln Trp Thr Asn Cys Gly Asn
             40              45                  50

Phe Val Ala Gly Lys Gly Trp Ser Thr Gly Asp Gly Asn Val Arg Tyr Asn Gly
 55              60                  65                  70

Tyr Phe Asn Pro Val Gly Asn Gly Tyr Gly Cys Leu Tyr Gly Trp Thr Ser Asn
         75              80              85                      90

Pro Leu Val Glu Tyr Tyr Ile Val Asp Asn Trp Gly Ser Tyr Arg Pro Thr Gly
             95                  100             105

Thr Tyr Lys Gly Thr Val Ser Ser Asp Gly Gly Thr Tyr Asp Ile Tyr Glu Thr
     110             115                 120                 125

Thr Arg Tyr Asn Ala Pro Ser Val Glu Gly Thr Lys Thr Phe Gln Gln Tyr Trp
             130             135                 140

Ser Val Arg Gln Ser Lys Val Thr Ser Gly Ser Gly Thr Ile Thr Thr Gly Asn
 145             150                     155             160

His Phe Asp Ala Trp Ala Arg Ala Gly Met Asn Met Gly Gln Phe Arg Tyr Tyr
         165             170                 175                 180

Met Ile Met Ala Thr Glu Gly Tyr Gln Ser Ser Gly Ser Ser Asn Ile Thr Val
             185                 190             195

Ser Gly
    200
```

XYLANASE FOR BIOBLEACHING

FIELD OF THE INVENTION

This invention relates to a high-specific activity xylanase enzymes from *Streptomyces lividans,* and in particular, to the application of these enzymes to lignocellulosic materials.

DESCRIPTION OF THE RELATED ART

The cohesion of a plant cell wall is primarily due to the presence of its principal components; a crystalline polymer, cellulose, and a three-dimensional macromolecule, lignin, which together comprises a lignocellulosic material. This lignocellulosic material is embedded in a matrix of pectic and hemicellulosic polysaccharides of various nature.

It is generally accepted that the relations that exist between these different polymers are established through linkages of different chemical nature. For instance, blocks of lignin are associated through hemicellulose chains. The hemicelluloses, another major component of lignocellulosic material, consist largely of 4-O-methylglucuronoxylan, which includes the $\beta$-1,4-linked polymer of D-xylose, and herein referred to as xylan. Generally, hardwood pulps contain larger amounts of xylan than do softwood pulps Such xylan can be enzymatically hydrolyzed to xylose by an endo-xylanase, $\beta$-1,4-D-xylan xylanohydrolase, denoted EC 3.2.1.8.

It has been previously shown that the partial or total digestion of xylan contained in lignocellulosic materials through the use of endo-xylanases, provides an attractive alternative to the totally mechanical and/or chemical process for the production of pulps, having improved pulp properties such as, for example, improved bleachability, or higher brightness. The use of xylanase for the improvement of pulp properties, and in particular, the improvement in brightness, has been termed "biobleaching".

Xylanase treatment of pulps, and in particular chemical pulps, has been shown to provide a biobleaching process which is capable of increasing both the brightness and the viscosity of the treated pulp, together with a decrease in the consumption of chlorine and other bleaching agents in subsequent bleaching stages. Thus, treatment with xylanase has been shown to improve pulp properties and to reduce the environmental impact of the bleaching process, when compared to conventional pulp bleaching processes not employing an endo-xylanase treatment.

Further, it has also been shown that because the release of lignin by hemicellulose cleavage has to be specific in order to prevent the deterioration of certain pulp qualities, e.g. viscosity, that may occur due to cellulose hydrolysis by cellulases, a substantially cellulase-free xylanase mixture is generally preferred.

Various routes to produce xylanase enzymes are known in the biobleaching industry. However, a preferred method is through the use of a recombinant microorganism of, for example, the genus Streptomyces, that is capable of being cultured for the production of cellulase-free, endo-xylanase.

Although biobleaching has many advantages, it is not currently practiced commercially because of the high cost of the enzyme treatment Typically, this high cost of treatment results because of the low activity of the endo-xylanase materials currently available.

Enzymes are proteins that act as catalysts in biological reactions. A simple way of illustrating the catalytic activity of an enzyme is by means of its specific activity expressed as IU/mg, which is the amount of product formed per quantity of enzyme used. The term IU (International Unit) refers to the amount of enzyme which catalyzes the transformation of 1 mass unit of substrate per minute under defined conditions of pH and temperature.

To date, the xylanases described in literature have specific activities ranging from as low as 8 to a maximum of 3,500 IU/mg of purified enzyme. At this activity level, the dosages of enzyme required to achieve a desired effect, is prohibitively expensive.

Surprisingly, we have now discovered and purified an endo-xylanase from the genus Streptomyces, and more specifically, from the species *Streptomyces lividans* that has a specific activity much greater than the activity of the previously known endo-xylanases.

In particular, the endo-xylanases of the present invention allow greatly reduced levels of xylanase to be utilized during biobleaching.

It is thus desirable to provide a endo-xylanase having a specific activity greater than the specific activity of previously known endo-xylanases. It is a further desired to provide a recombinant microorganism of the genus Streptomyces that is capable of being cultured for the production of cellulase-free, high-activity endo-xylanase. It is still further desired to provide a method of treating lignocellulosic material, and in particular a chemical pulp, with the high specific activity endo-xylanase.

SUMMARY OF THE INVENTION

Accordingly, the present invention provides a high-activity endo-xylanase obtained naturally from a strain of the genus Streptomyces, or from a recombinant microorganism produced by the introduction of a hybrid plasmid into a host microorganism mutant strain of the genus Streptomyces, said hybrid plasmid being constructed by the insertion of a novel xylanase gene, denoted as xln C, obtained from a xylanase gene-containing microorganism of the genus Streptomyces, into a vector plasmid.

Preferably, the vector plasmid is obtained from a microorganism of the genus Streotomyces. A preferred species of Streptomyces of use in the present invention is *Streptomyces lividans.*

A high-activity endo-xylanase is defined as a xylanase which has a specific activity of greater than 5,000 IU/mg of purified protein, according to the BioRad TM's protein measurement technique. More preferably, the specific activity of the endo-xylanase is greater than 20,000, and even more preferably greater than 30,000 IU/mg, and still more preferably greater than 40,000IU/mg.

Although the measured specific activity of the xylanase may vary depending on the specific test method utilized, it should be noted that, as described hereinbelow, the amount of xylanase required for biobleaching is less than the amounts previously utilized.

Preferably, the endo-xylanase is substantially cellulase-free. By the term "substantially cellulase-free" is meant those systems which do not contain sufficient amounts of cellulase to effect the unfavourable hydrolysis of glucosidic linkages present in the cellulose when the enzyme is applied to cellulose pulps.

It is also preferable that the endo-xylanase is obtained from a host microorganism wherein the host microorganism mutant strain is characterized by it having a cellulase-negative activity Cellulase-negative, when used in this context, is defined as a strain which produces a cellulase-free xylanase which is essentially free from extracellular cellulase.

Further, it is also preferable that the endo-xylanase is obtained from a host microorganism wherein the host microorganism mutant strain is characterized by it having a xylanase-negative activity. Xylanase-negative, with respect to the host microorganism, is defined as a strain which prior to the introduction of the hybrid plasmid, would produce an enzyme(s) essentially free from xylanase.

Even more preferably, the endo-xylanase is obtained from a host microorganism wherein the host microorganism is characterized by having both cellulase-negative and xylanase-negative activity.

In a further aspect, the invention provides a recombinant microorganism which contains a hybrid plasmid that carries the xln C gene that codes for the production of the high-activity xylanase C enzyme, wherein said plasmid is capable of inducing the extracellular production of high-activity endo-xylanase in a host microorganism into which said plasmid has been introduced.

Preferably, the recombinant microorganism contains a hybrid plasmid which is capable of inducing the extracellular production of a cellulase-free, high activity endo-xylanase, free of extracellular cellulase.

Further, the recombinant microorganism is obtained from a host microorganism wherein said host microorganism is a mutant strain of the genus Streptomyces, and preferably from the species *Streptomyces lividans.*

The present invention also provides a recombinant microorganism obtained from a host microorganism wherein the host microorganism is characterized by having cellulase-negative and/or xylanase-negative activity.

Accordingly, the host microorganism is preferably a mutant strain of the species *Streptomyces lividans,* wherein said host microorganism is characterized by having cellulase-negative activity. More preferably, the host microorganism is a double mutant strain of the genus Streptomyces wherein said host microorganism is characterized by having xylanase-negative activity.

Yet more preferably the host microorganism is a double mutant strain of the species *Streptomyces lividans,* said strain characterized by it having also xylanase-negative activity.

Still yet more preferably the host microorganisms is the double mutant strain *Streptomyces lividans* 10-164 and the host microorganism is characterized by cellulase-negative and xylanase-negative activities.

It should be noted that a host microorganism mutant strain characterized by it having xylanase-negative and/or cellulase-negative activity, as described hereinabove with respect to the present invention, includes those mutant strains that may also have other enzyme-negative activities.

In yet a further aspect, the invention provides a hybrid plasmid constructed by the insertion of the xylanase C (xln C) gene into a vector plasmid. Preferably, either or both of said gene and said vector plasmid are obtained from microorganisms of the genus Streptomyces. More preferably, either or both of the xylanase C (xln C) gene or the vector plasmid are obtained from microorganisms of the species *Streptomyces lividans.* Most preferably, the xylanase C (xln C) gene is obtained from the strain *Streptomyces lividans* 1326 and/or the vector is pIJ702 obtained from the strain *Streptomyces lividans* 3131.

In a still further aspect, the present invention provides a xylanase gene, denoted as xln C, coded for the DNA sequence comprised essentially of the sequence set out in Table 1.

In still yet a further aspect, the invention provides a method for the production of a recombinant microorganism hereinabove defined, comprising the introduction of a hybrid plasmid, defined hereinabove with respect to the present invention, into a host microorganism, also as defined hereinabove.

The hybrid plasmid may be introduced into the host microorganism by the technique of protoplast fusion or electro-fusion, preferably by transduction or more preferably by transformation.

The xylanase C (xln C) gene is said to have been cloned upon its introduction into the host microorganism, hereinabove defined, thus providing a recombinant microorganism characterized by at least its high-activity endo-xylanase with a cellulase-negative activity. The expression of the xln C gene in the recombinant microorganism results in the production of cellulase-free, high-activity endo-xylanase.

By molecular cloning and advanced fermentation technology, improved production of this novel enzyme in a cellulase-free *Streptomyces lividans* host can be achieved, and the enzyme produced was found to be of value for pulp treatment.

The endo-xylanase is secreted extracellularly into a culture medium of the recombinant microorganism in the presence of a suitable growth medium containing a suitable carbon source for the expression of the enzyme. Preferably the xylanase is an endo-xylanase, also referred to as xylanase or β-1,4-D-xylan xylanohydrolase, designated EC 3.2.1.8, characterized as being substantially cellulase-free and possessing high specific activity.

TABLE 1
Xylanase C DNA Sequence

```
                                                              CTGCTGCTGCCCGGCACAGCCCACGCC
                                                               L   L   L   P   G   T   A   H   A
                                                                              -10
GCCACTACCATCACCACCAACCAGACCGGCACCGACGGCATGTACTACTCGTTCTGGACCGACGGCGGCGGC
 A   T   I   L   T   N   Q   T   G   T   D   G   M   Y   Y   S   F   W   T   D   G   G   G
-20                              10                                  20
TCCGTCTCCATGACGCTCAACGGTGGCGGCAGCTATAGCACCCAGTGGACCAACTGCGGCAACTTCGTCGCC
 S   V   S   M   T   L   N   G   G   G   S   Y   S   T   Q   W   T   N   C   G   N   F   V   A
+1                   30                                  40
GGCAAGGGCTGGAGCACCGGCGACGGCAACGTCCGCTACAACGGCTACTTCAACCCCGTCGGCAACGGCTAC
 G   K   G   W   S   T   G   D   G   N   V   R   Y   N   G   Y   F   N   P   V   G   N   G   Y
             50                                  60                                  70
GGCTGCCTCTACGGCTGGACCTCGAACCCGCTGGTGGAGTACTACATCGTCGACAACTGGGGCAGTTACCGG
 G   C   L   Y   G   W   T   S   N   P   L   V   E   Y   Y   I   V   D   N   W   G   S   Y   R
                     80                                  90
CCCACCGGTACGTACAAGGGCACCGTCTCCAGCGACGGAGGCACCTACGACATCTACCAGACGACCCGGTAC
 P   T   G   T   Y   K   G   T   V   S   S   D   G   G   T   Y   D   I   Y   Q   T   T   R   Y
             100                                 110                                 120
AACGCCCCCTCCGTGGAAGGCACCAAG ACCTTCCAGCAGTACTGGAGTGTCCGG CAGTCGAAGGTGACCAGT
 N   A   P   S   V   E   G   T   K   T   F   Q   Q   Y   W   S   V   R   Q   S   K   V   T   S
                     130                                 140
GGCTCCGGCACCATCACCACCGGCAACCACTTCGACGCCTGGGCGCGCGCGGGCATGAACATGGGCCAGTTC
 G   S   G   T   I   T   T   G   N   H   F   D   A   W   A   R   A   G   M   N   M   G   Q   F
             150                                 160
AGGTACTACATGATCATGGCCACCGAG GGCTATCAGAGCAGTGGAAGCTCGAACATCACGGTCAGCGGTTGA
 R   Y   Y   M   I   M   A   T   E   G   Y   Q   S   S   G   S   S   N   I   T   V   S   G   —
     170                                 180                                 190
CCTCTGGCCGGTGGACGACGGGGCGTG GGCCGTCTACGTGGCGGGCCAACAACTGTGGTCGCATTGCTGGGA
```

The enzymatic degradation of the xylan by hydrolysis of the xylan linkages is partial and thus there is no drastic release of xylose and xylobiose from the pulp.

According to the present invention, the treatment of lignocellulosic material, preferably a chemical pulp, by high-activity endo-xylanase that is cellulase-free results in delignification (as noted by a reduction in the Kappa number value of treated pulps), brightening and viscosity improvement. Further, such treatment may provide more relaxed fibres resulting in improved performance of a subsequent treatment, such as swelling, beating, drainage or chemical bleaching of the pulp with an overall reduction in energy and chemicals used.

Because of the high activity of the xylanase of the present invention, it is particularly well suited for use in the biobleaching of pulp. Accordingly, in a further aspect the invention provides a method of treating pulp, and preferably a chemical pulp, having xylanase-hydrolyzable β-1,4-D-xylosidic linkages, said method comprising contacting said pulp with a high-activity endo-xylanase as described hereinabove, to effect hydrolysis of said linkages. Preferably, the hydrolysis of said linkages will result in the biobleaching of said pulp.

The level of the endo-xylanase required for biobleaching is significantly less than the level of xylanase required in prior art processes. Preferably, the endo-xylanase of the present invention is used at a level of less than 0.1 mg of xylanase per gram of pulp (w/w) expressed as oven dried pulp. More preferably, the level of endo-xylanase is less than 0.01 mg/g pulp, and still more preferably, the level of endo-xylanase is less than 0.005 mg/g of pulp.

The method of the present invention, may also be used to treat an aqueous northern or southern hardwood pulp slurry with two different cellulase-free xylanases.

While it is preferred to employ a kraft pulp, other chemically digested pulps may be used. The pulp can also be oxygen-treated prior to the treatment. The unbleached kraft pulp may be treated in one or more separate stages, and may be used in combination with a low activity enzyme treatment stage. For example, a lower-specific activity endo-xylanase from *Streptomyces lividans*, could be used in a first stage, and the high-activity xylanase C from *Streptomyces lividans* in accordance with the present invention, such as [pIAF20], described hereinbelow, for example, could be used in a second stage.

The concentration of enzyme during treatment typically ranges from about 0.01 to 500 IU/g of treated pulp, and preferably between 1 and 500 IU/g, depending on the degree of biobleaching and/or delignification desired, and the treatment is conducted at a temperature of from about 20° C. to about 80° C., preferably 50° C. Both supernatants are preferably free of cellulase activity and therefore provide for a specific attack of the xylans contained in the pulp.

During treatment with the endo-xylanase, the consistency of the pulp is preferably from about 0.1 % to about 30%, based on the oven-dry weight of the pulp. A consistency of from about 2% to about 12% is preferred. The mixture can be agitated at various speeds with the use of various mixing devices. The pulp is subsequently treated in various ways depending upon the type of paper product desired.

DESCRIPTION OF THE PREFERRED EMBODIMENTS

In a preferred embodiment of the present invention, an extracellular high-activity endo-xylanase (referred herein as xylanase C), produced from *Streptomyces lividans* 66, was purified by anion-exchange chromatography and its activity tested on xylan from birch wood or oat spelt using the DNS method previously described by Morosoli et al., Biochem. J.; 239, 587, 1986. The gene coding for the production of the xylanase C is also cloned through functional complementation of a xylanase- and cellulase-negative mutant using the multicopy vector pIJ702. The new clone, once grown in a fermenter, produced an extracellular xylanase C and no cellulase was detected The activity of the new enzyme was measured at 45,450 IU/mg of purified protein according to the BioRad TM's protein measurement technique. The activity of this enzyme constitutes a tremendous increase over all other xylanases reported to date.

This new enzyme was used and compared, in a bleaching experiment, to a lower-specific activity type endo-xylanase enzyme, designated as xylanase A, as described by Morosoli et al., Biochem. J.; 239,587, 1989, also expressed by *Streptomyces lividans* 66, and having an activity of 733 IU/mg of purified enzyme, and which is typical of the enzymes of the prior art.

Surprisingly, xylanase C reduced the lignin content of pulp (measured as its Kappa number value) to a lower value than the lower-specific activity enzyme at a dosage of 0.0019 mg of enzyme/g of treated pulp, as compared to 0.12 mg of enzyme/g of treated pulp for the low-specific activity endo-xylanase (xylanase A). This constitutes a 61 fold improvement in efficiency of the xylanase C enzyme over the xylanase A, both expressed from *Streptomyces lividans*.

The high-activity endo-xylanase is purified and characterized as follows. The *Streptomyces lividans* 66 strain is maintained on 7-day old agar slant cultures containing a modified yeast-extract malt-extract medium where glucose is substituted by 0.4% of maltose. Spore suspensions prepared from such slants are used as inocula for vegetative cultures in Trypticase Soy Broth (TSB)(Difco Laboratories, Detroit, Mich.). The flask cultures are incubated at 34° C. on a rotary shaker at 240 rpm for a period of 24–30 h.

Enzyme production is carried out in 500-ml Erlenmeyer flasks containing 100 ml of M-13 medium, previously described by Bertrand et al., (Biotechnol. Bioeng.; 33, 791, 1989) using 1% xylan from oat spelt as main carbon source. The inoculum size is 5% of the vegetative TSB culture and in the incubation time is set at 72 hours. The crude enzyme is recovered from the supernatant by centrifugation of the fermentation broth in a Beckman J2-21 centrifuge at 11,000 g. From this supernatant, the xylanase C is precipitated with three volumes of cold ethanol. After settling overnight, the precipitate is recovered by centrifugation at 11,000 g.

The sedimented crude enzyme is recovered, washed thoroughly with acetone and dried under vacuum overnight. The dried powder obtained in this manner can be stored without loss of activity at 4° C. for several months. For purification of the xylanase C, 30 g of the crude enzyme preparation are dissolved by slow agitation for 10 minutes in 500 ml of 50mM sodium phosphate buffer, pH 7.4, and centrifuged at 11,000 g to remove residual undissolved material.

The solution is cooled on ice and the xylanase C fraction is obtained by ammonium sulphate precipitation at 45%. The precipitate is redissolved in the sodium phosphate buffer and dialyzed against distilled water in cellophane tubing with a cut-off of 6,000 to 8,000 Da which is treated with 1 mM EDTA and 2% sodium bicarbonate for 10 minutes, at 100° C. The enzyme solution is concentrated by lyophilisation, redissolved in 20 mM Tris-HCl buffer at pH 8.5 and filtered through an Acro TM 0.2 μm disposable filter assembly (Gelman Sciences, inc., Ann Arbor MI.). The filtrate is absorbed directly onto an anion-exchange DEAE Protein Pak 5 PW semi-preparative H.P.L.C. column (Waters-Millipore Inc., St. Laurent, Que.) which is equilibrated with the same Tris-HCl buffer. The elution is carried out using a linear gradient of 1M NaCl and is monitored with an U.V. recorder set at 280 nm. Fractions are collected and the enzyme activity detected by the Remazol Brilliant Blue (Kluepfel, RBB Method, Methods in Enzymology, Vol. 160, p180, 1988). The active fractions are pooled, dialyzed against water at 4° C. for 65 hours. The pure enzyme is recovered after freeze-drying of this aqueous solution. To verify homogeneity, the enzyme is passed through two Superose 6 TM gel columns equilibrated with 0.1M ammonium acetate at pH 6.0. The extracellular high-activity xylanase C has an apparent $M_r$ of 22,000 daltons and pI superior to 10.5. The protein is apparently not glycosylated.

Enzymatic activity is determined by using xylan from birch wood (Sigma Chem. Co., St. Louis, Mo.) dissolved in 50mM sodium citrate buffer, and the reducing sugars determined by the dinitrosalicylic acid (DNS) method.

All enzyme activities are expressed in international units (IU), where 1 unit is defined as the amount of enzyme that releases 1 μmol of reducing sugars (expressed as xylose) in 1 min.

Streptomyces lividans [pIAF20] containing the high-activity endo-xylanase C is obtained by cloning the xln C gene of Streptomyces lividans 66 (strain 1326) using the multicopy vector pIJ702 by functional complementation in Streptomyces lividans 10-164, a xylanase- and cellulase-negative mutant, obtained by mutation of the wild-type strain 1326 with N-methyl-N'-nitro-N-nitrosoguanidine. Xylanase C-harboring clone Streptomyces lividans [pIAF20] is detected by the formation of a clearing zone on a xylan-containing Petri plate. Plasmid DNA purifications are performed by the alkaline method of Kendall and Cullum (Gene; 29, 315, 1984) and hybrid plasmids are analyzed by the micro-technique of Thompson et al. (Mol. Gen. Genet.; 195, 39, 1982). The recombinant plasmid obtained after cloning contains a large DNA insert of 7.5 Kb in length. Subcloning and sequencing experiments localized the gene more precisely on the PstI-BamHI fragment.

The methods for the construction of the hybrid plasmid and the treatment of lignocellulosic material with the high-activity xylanase, will now be demonstrated by way of example only, with reference to the following examples.

EXAMPLE 1

A xylanase producing clone was prepared according to the following procedure.

Chromosomal DNA was extracted from Streptomyces lividans 66 (strain 1326) according to the method of Hopwood et al. (Genetic Manipulation of Streptomyces, A laboratory manual., The John Innes Foundation, Norwich, UK 1985). Agarose gel electrophoresis of restriction fragments was performed using Tris-borate-EDTA buffer (Maniatis et al., (Molecular Cloning, A Laboratory Manual, Cold Spring Harbor, N.Y., 1982) and Southern blotting and hybridization conditions were as described by Hopwood et al. (1985). The strain Streptomyces lividans 1326 was then mutated by using N-methyl-N'-nitro-N-nitrosoguanidine (Delic et al., Mutation Res.; 9, 167 (1970)), and a double mutant β-1,4-D-glucan glucanohydrolase (endocellulase)-negative and xylanase-negative was selected. The double mutant was selected on a solid minimal medium containing 1% carboxymethyl-cellulose as main carbon source.

Visualization of endocellulase activity was achieved by Congo Red staining according to Teather and Wood (Appl. Environ. Microbiol.; 43, 777, 1982). The detection of xylanase-negative mutants was carried out in the same manner substituting the carboxymethyl-cellulose by 1% oat spelts xylan. The Congo Red coloration was found to be applicable also for the detection of xylanase activity. In both cases, the absence of decoloration zones was taken as an indication for the absence of enzyme production.

The double mutant, designated as Streptomyces lividans 10-164 was found to be very stable, and appeared to give the highest transformation efficiency. Therefore it was selected as the host microorganism for the development of the expression system. Protoplasting and transformation of the double mutant Streptomyces lividans 10-164 was performed as described by Chater et al. (Curr. Topics Microbiol. Immunol.; 97, 69, 1982).

A xylanase-producing clone was selected and designated Streptomyces lividans [pIAF20]. It was shown to differ from the previously reported xylanase A and xylanase B genes (Mondou et al., Gene: 49, 323, 1986 and Vats-Mehta et al., Gene; 86, 119, 1990 respectively) by its restriction map and by Southern blotting and DNA hybridization. As was the case with xylanase B, earlier investigations on the wild-type strain Streptomyces lividans 1326 had not revealed the presence of xylanase C in its supernatant.

Its biosynthesis in this strain could be demonstrated only by Western blots once anti-(xylanase C) antibodies, raised in rabbits with the enzyme isolated from culture filtrates of clone Streptomyces lividans [pIAF20], were used.

EXAMPLE 2

The xln C gene was cloned in plasmid pIAF20 on a 2.3 Pstl fragment. Standard DNA recombinant techniques and cloning into M13 phages were as described by Hopwood et al., (1985) and/or Maniatis et al., (1982). Fragments of interest were subcloned into M13mp18 or M13mp19 bacteriophages.

Nt sequence determination was carried out according to the chain-terminating dideoxy method of Sanger et al., (Proc. Natl. Acad. Sci. U.S.A.; 74, 5463, 1977) using deleted fragments of the inserts obtained by the method of Dale et al., (Plasmid; 13, 31, 1985). Occasionally synthetic oligonucleotides were used as primers and 7-deaza-dGTP was used to reduce band compressions. Computer analysis of DNA sequences were carried out using the Pustell Sequence Analysis Programs of International Biotechnologies Inc. (New Haven, Conn., U.S.A.).

As described hereinabove, the xylanase C DNA sequence is shown in Table 1.

EXAMPLE 3

Two supernatants of a recombinant *Streptomyces lividans* clone containing respectively the high-activity endo-xylanase derived from the xln C gene, and a low-active endo-xylanase derived from the xln A gene (both genes from *Streptomyces lividans* and both β-1,4-D-xylan xylanohydrolases EC 3.2.1.8) were used to treat a kraft hardwood pulp sample.

The treatment conditions were as follows:

| Initial Kappa number: | 13.5 | |
|---|---|---|
| Enzyme Dosage: | xylanase A | 0.116 mg/g of pulp |
| | xylanase C | 0.0019 mg/g of pulp |

Treated and control samples (5 g O.D. each) were suspended in 83.3 ml of 4.5mM Citrate/16mM Phosphate buffer at pH 6.0 and incubated at 50° C. for 2 hours in a rotary shaker at 300 rpm. Upon completion of the xylanase treatment, the pulp samples were washed with distilled water. The Kappa number, as an indication of delignification, was measured using a standard TAPPI test method. The results are listed in Table 2 together with the Kappa No.s for the untreated pulp, and a pulp sample which was subjected to the buffer solution only, as a control.

TABLE 2

Comparison of xylanases A and C on kraft pulp

| Treatment | Kappa No. |
|---|---|
| Original pulp | 13.5 |
| Buffer Control | 12.3 |
| | 12.4 |
| Xylanase A | 10.3 |
| | 10.3 |
| Xylanase C | 9.6 |
| | 9.8 |

It was thus demonstrated that both enzymes, used at an equivalent dose (IU/g of pulp) basis, were approximately equally effective in reducing the lignin content as measured by Kappa numbers. However, the weight of the amount of xylanase C required was significantly less than the amount of xylanase A required.

EXAMPLE 4

A hardwood kraft pulp was treated with 85 IU/g of xylanase A and subsequently bleached using a $D_cE_oDED$ sequence. The enzymatic treatment conditions were; consistency 6%, temperature of 50° C., treatment time of 2 hours, pH 5.5–6.0. As a control, an untreated same of the same pulp was bleached using the same sequence, to a similar brightness level. The conditions used for the bleaching and biobleaching processes are set out in Table 3.

TABLE 3

| CONDITIONS | Bleaching Conditions | | | | |
|---|---|---|---|---|---|
| | $D_c$* | $E_o$ | D | E | D |
| Non-enzymatic treatment | | | | | |
| Charge (% on pulp) | 2.4 | 0.4 | 1.2 | 0.6 | 0.4 |
| Consistency (% w/w) | 3.5 | 10 | 10 | 0.6 | 10 |
| Temperature (°C.) | 50 | 65 | 80 | 65 | 80 |
| Time (min) | 20 | 60 | 75 | 60 | 75 |
| Enzymatic treatment | | | | | |
| Charge (% on pulp) | 1.3 | 0.4 | 1.2 | 0.6 | 0.4 |
| Consistency (% w/w) | 3.5 | 10 | 10 | 0.6 | 10 |
| Temperature (°C.) | 50 | 65 | 80 | 65 | 80 |
| Time (min) | 20 | 60 | 75 | 60 | 75 |

*70% $ClO_2$; 30% $Cl_2$ substitution

The chlorine charge was reduced from 0.86 to 0.36 and chlorine dioxide charge was reduced from 2.36 to 1.01.

Recent research has linked the level of AOX (Absorbable Organic Halide) formation with the chemical charge, particularly chlorine. AOX is a standard measure accepted in the industry for determining the content of chlorinated organics in bleach plant effluents. This class of compounds has been associated with environmental toxicity and it is believed that the concentration of AOX present in effluents is directly linked to the quantity of chlorinated bleaching compounds used in the bleaching process. Presently, the global community aims at establishing a maximum permissible limit to reduce the present concentration. Therefore, a method to reduce AOX is desirable.

An estimate of AOX formation can be calculated according to the following equation proposed by Reeve, D. W. and Earl, P. I., (Proc. Tappi Environ. Conf., Atlanta, p. 385, 1989):

$$AOX = 0.1\ (Cl_2 + 0.526 * ClO_2)\text{kg } C_l/\text{te pulp}$$

Thus, the AOX level for enzyme treated pulp followed by the sequence $D_cE_oDED$ (where $D_c$ is a chlorine dioxide stage with 30% chlorine substitution, E is a caustic extraction) was 0.89 kg Cl/te pulp whereas for non-enzyme-treated pulp an AOX level of 2.10 Kg Cl/te. Accordingly, the use of xylanase was responsible for lowering levels of AOX more than 2 fold.

Example 3 thus clearly illustrates the utility of the invention in reducing the overall bleach consumption and subsequently AOX concentration.

Having described specific embodiments of the present invention, it will be understood that modifications thereof may be suggested to those skilled in the art, and it is intended to cover all such modifications as fall within the scope of the appended claims.

---

The embodiments of the invention in which an exclusive property or privilege is claimed are defined as follows:

1. An isolated and purified high-activity endo-xylanase which has a specific activity of greater than 5,000 IU/mg of purified protein, an apparent Mr of 22,000 daltons as measured by SDS polyacrylamide gel electrophoresis, and a pI greater than 10.5 and which is obtained from a strain of the species *Streptomyces lividans*, or from a recombinant microorganism produced by the introduction of a hybrid plasmid into a host microorganism mutant strain of the genus Streptomyces, said hybrid plasmid being constructed by the insertion of a xylanase gene, denoted as xln C, obtained from a xylanase gene-containing microorganism of the species *Streptomyces lividans*, into a vector plasmid.

2. A high-activity endo-xylanase as claimed in claim 1 which has a specific activity of greater than 20,000 IU/mg.

3. A high-activity endo-xylanase as claimed in claim 1 which has a specific activity of greater than 30,000 IU/mg.

4. A high-activity endo-xylanase as claimed in claim 1 which has a specific activity of greater than 40,000 IU/mg.

5. A high-activity endo-xylanase as claimed in any one of claims 1 or 2 to 4 wherein said vector plasmid is obtained from a microorganism of the genus Streotomyces.

6. A high-activity endo-xylanase as claimed in any one of claims 1 or 2 to 4 which is substantially cellulase-free.

7. A high-activity endo-xylanase as claimed in any one of claims 1 or 2 to 4 wherein the host microorganism mutant strain is characterized by it having a cellulase-negative activity.

8. A high-activity endo-xylanase as claimed in any one of claims 1 or 2 to 4 wherein the host microorganism mutant strain is characterized by it having a xylanase-negative activity.

9. A high-activity endo-xylanase as claimed in any one of claims 1 or 2 to 4 wherein the host microorganism mutant strain is characterized by it having a cellulase-negative and xylanase-negative activity.

10. A high-activity endo-xylanase as claimed in any one of claims 1 or 2 to 4 wherein said endo-xylanase is obtained from a strain from the specific *Streptomyces lividans*.

* * * * *